(12) United States Patent  (10) Patent No.: US 8,535,378 B2
Jackson  (45) Date of Patent: Sep. 17, 2013

(54) VERTEBRAL INTERBODY SPACER

(76) Inventor: Roger P. Jackson, Prairie Village, KS (US)

( * ) Notice: Subject to any disclaimer, the term of this patent is extended or adjusted under 35 U.S.C. 154(b) by 1072 days.

(21) Appl. No.: 10/842,295

(22) Filed: May 10, 2004

(65) Prior Publication Data

US 2005/0251258 A1    Nov. 10, 2005

(51) Int. Cl.
*A61F 2/44* (2006.01)
(52) U.S. Cl.
USPC ........................................................ 623/17.11
(58) Field of Classification Search
USPC ........................................................ 623/17.11
See application file for complete search history.

(56) References Cited

U.S. PATENT DOCUMENTS

| | | | |
|---|---|---|---|
| 4,834,757 A | 5/1989 | Brantigan | |
| 4,863,477 A * | 9/1989 | Monson | 623/17.12 |
| 5,139,527 A | 8/1992 | Redl et al. | |
| 5,425,772 A | 6/1995 | Brantigan | |
| 5,443,514 A | 8/1995 | Steffee | |
| 5,458,638 A | 10/1995 | Kuslich et al. | |
| 5,489,308 A | 2/1996 | Kuslich et al. | |
| 5,534,030 A * | 7/1996 | Navarro et al. | 623/17.15 |
| 5,554,191 A | 9/1996 | Lahille et al. | |
| 5,609,636 A | 3/1997 | Kohrs et al. | |
| 5,658,337 A | 8/1997 | Kohrs et al. | |
| 5,665,122 A | 9/1997 | Kambin | |
| 5,669,909 A | 9/1997 | Zdeblick et al. | |
| 5,681,135 A | 10/1997 | Simonson | |
| 5,693,100 A | 12/1997 | Pisharodi | |
| 5,716,355 A | 2/1998 | Jackson et al. | |
| 5,716,415 A | 2/1998 | Steffee | |
| 5,782,919 A | 7/1998 | Zdeblick et al. | |
| 5,865,847 A | 2/1999 | Kohrs et al. | |
| 5,904,719 A | 5/1999 | Errico et al. | |
| 5,941,880 A | 8/1999 | Errico et al. | |
| 5,968,098 A | 10/1999 | Winslow | |
| 5,980,522 A | 11/1999 | Koros et al. | |
| 6,053,916 A | 4/2000 | Moore | |
| 6,059,829 A * | 5/2000 | Schlapfer et al. | 623/17.16 |
| 6,102,950 A | 8/2000 | Vaccaro | |
| 6,117,174 A | 9/2000 | Nolan | |
| 6,123,705 A | 9/2000 | Michelson | |
| 6,129,763 A | 10/2000 | Chauvin et al. | |
| 6,162,252 A * | 12/2000 | Kuras et al. | 623/17.16 |
| 6,165,219 A | 12/2000 | Kohrs et al. | |
| 6,176,882 B1 | 1/2001 | Biedermann et al. | |
| 6,206,922 B1 | 3/2001 | Zdeblick et al. | |
| 6,224,631 B1 | 5/2001 | Kohrs | |
| 6,325,827 B1 | 12/2001 | Lin | |
| 6,436,139 B1 | 8/2002 | Shapiro et al. | |
| 6,440,170 B1 | 8/2002 | Jackson | |
| 2003/0023306 A1 * | 1/2003 | Liu et al. | 623/17.11 |
| 2003/0208271 A1 * | 11/2003 | Kuras | 623/17.11 |
| 2004/0199251 A1 * | 10/2004 | McCombe et al. | 623/17.11 |

* cited by examiner

*Primary Examiner* — Bruce E Snow
*Assistant Examiner* — Melissa Hoban
(74) *Attorney, Agent, or Firm* — John C. McMahon

(57) ABSTRACT

A spinal fusion interbody spacer device has a solid central core positioned between laterally opening opposed concave side surfaces. The device includes spaced apart superior and inferior abutment surfaces which are convexly arced. The spacer device is implanted between a pair of adjacent vertebrae by insertion in a tipped-over orientation and then reoriented to an upright orientation for engagement of the abutment surfaces by facing surfaces of the vertebrae.

14 Claims, 3 Drawing Sheets

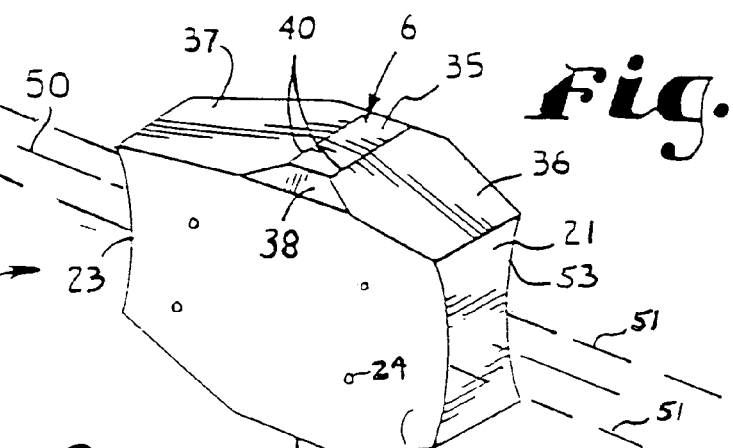
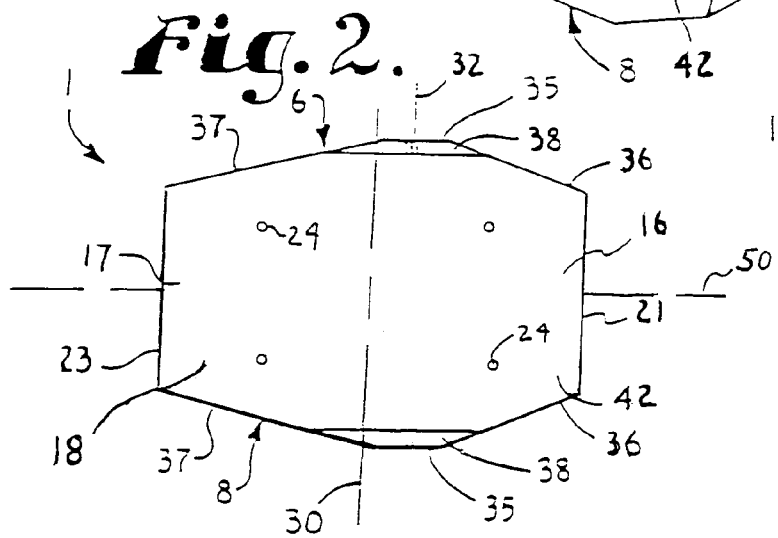
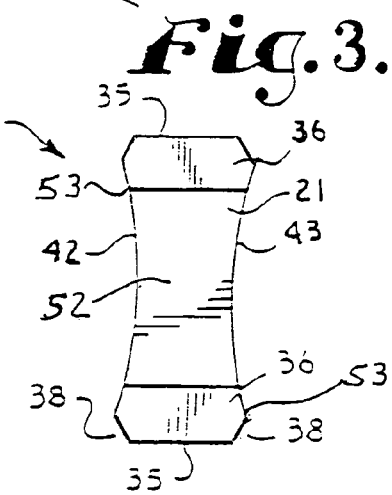
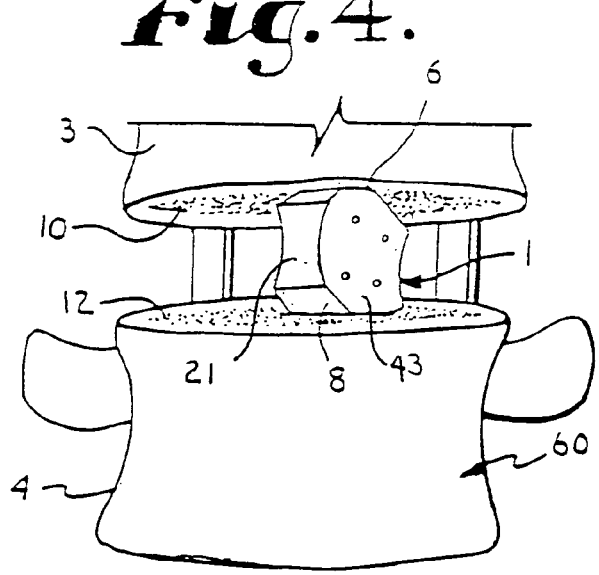
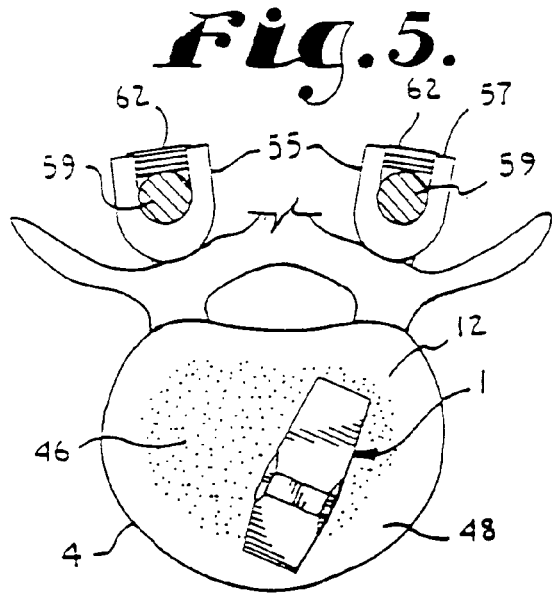

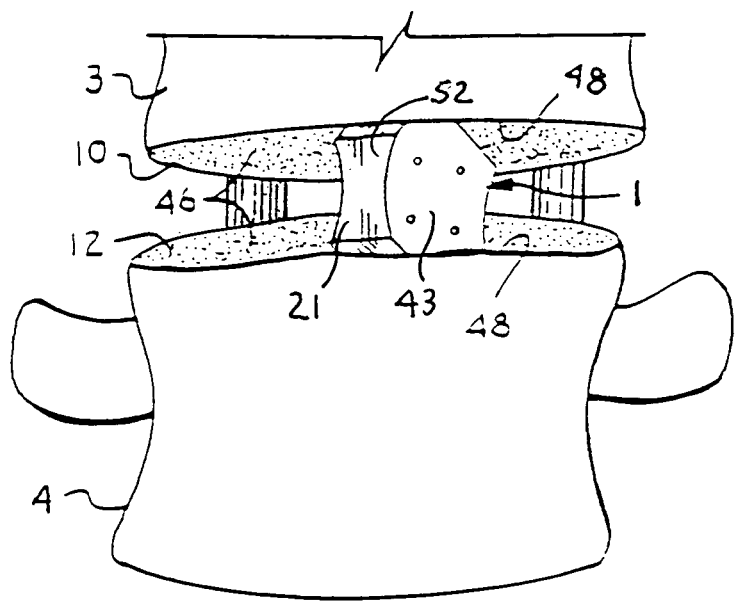
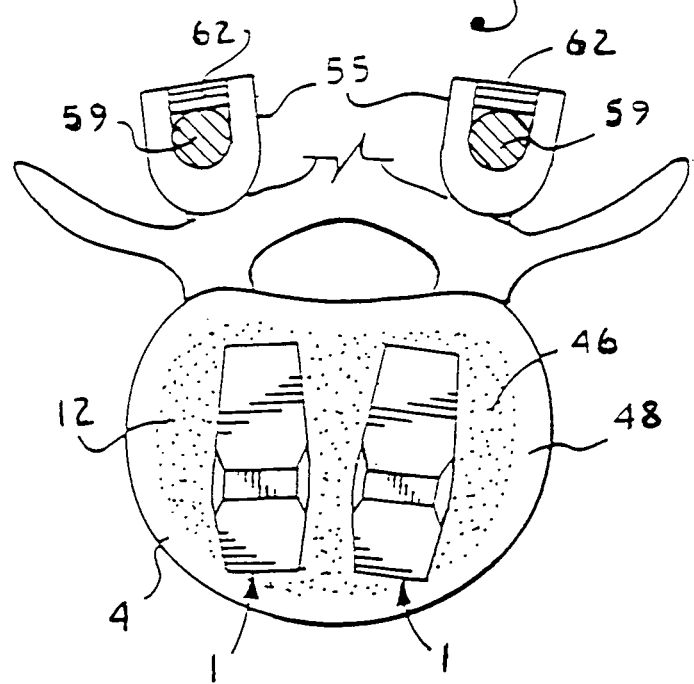

VERTEBRAL INTERBODY SPACER

CROSS REFERENCE TO RELATED APPLICATION

The present application is a continuation-in-part of Ser. No. 10/651,800 filed Aug. 29, 2003 entitled Threaded Interbody Device which is incorporated herein by reference.

BACKGROUND OF THE INVENTION

The present application is directed to an interbody device for implantation between a pair of adjacent vertebrae in order to provide support to the vertebrae and/or promote bone fusion between the vertebrae and, in particular, to a non threaded interbody device having opposed concave sides and a solid core.

In the human spine the pad or disc between vertebrae is sometimes damaged or deteriorates due to age, disease, injury, or congenital defect. The vertebrae may also become compressed or otherwise damaged. Vertebrae often become too closely spaced anteriorly due especially to age and other factors that generally produces an abnormal and undesirable curvature with respect to lordosis or kyphosis. Because of this, surgery is sometimes utilized to place spacers or interbody devices between the vertebrae which provide proper spacing of the vertebrae and which also promote fusion between the vertebrae. When a device of this type is utilized for purposes of promoting fusion, it is often referred to as an intervertebral fusion device. When utilized to promote fusion, bone pieces or bone growth promoting material is normally packed or placed between the vertebrae to promote growth of bone and, therefore, fusion between the vertebrae.

In the past, interbody devices have typically had a hollow central cavity and been either generally rectangular in shape or cylindrical in shape and threaded. The cylindrical devices also typically have passthrough perforations or fenestrations and are threadably received between as well as into the adjacent vertebrae. For placement of cylindrical devices, the vertebrae are typically first spaced apart to a desirable position, and then a drill is utilized to create a partial bore (radiused channel) in each vertebra which allows this type of interbody device to be received in the space between the vertebrae and partially into each vertebra. Because of the space between the bones, the interbody device usually engages the bones only along an upper surface and a lower surface thereof. When the interbody device is of a cylindrical threaded type, the upper and lower surfaces are radiused relative to a front to rear axis and such are essentially designed to engage the region of the vertebrae where bone is unremoved by boring. Such devices obviously require removal of bone, but it is preferred that the vertebrae be left as whole as possible so such removal is not desirable.

However, when interbody devices are used, it is desirable that the device engage as much surface of bone as possible to provide support to the bone and to reduce the likelihood of subsidence of the device into the bone. Such subsidence results from contact pressure of the interbody spacer relative to an engaging surface of a vertebra, since part of the bone is somewhat spongy in nature, especially near the center of the upper and lower surfaces of the bones. The remainder of the interbody device mainly functions to support the two surfaces. Because it is also desirable in such structures to maintain weight and volume as low as possible, in order to make the device more compatible with the body, it is also desirable to make the entire device as small and lightweight as possible, while maintaining strength. In the present application this is accomplished by use of a solid core with side surfaces that are concave facing laterally outwardly so as to produce upper and lower arches on each side that provide effective and efficient load bearing buttress structures that better distribute overall implant stresses thereby providing strong support to the vertebrae with comparatively less implant weight and volume.

As noted above, it is also desirable to minimize the amount of cutting into and reshaping of the vertebral bones to only that which is necessary to correct the structure and function of the spine. Thus, it is considered advantageous in the present invention to conform the interbody spacer to the shape of the intervertebral surfaces of adjacent vertebrae, which is shallowly concave, rather than conform the vertebrae to the shape of the interbody spacer.

As noted above, age and injury cause the vertebrae to somewhat anteriorly collapse over time. Therefore, it is preferred that such an interbody spacer correctly space the vertebrae anteriorly so as to promote normal lordosis or curvature with respect to the spine in the lower back or kyphosis in the upper back.

SUMMARY OF THE INVENTION

The present invention provides an interbody or intervertebral spacer device for placement between a pair of spaced, but adjacent and facing vertebrae. The spacer device is preferably generally convex or sloped between the anterior and posterior ends (that is between front and rear or along the longitudinal axis), preferably on both the top and bottom, so as to generally conform with both the concave shape of the surface of the vertebrae and the desired orientation and alignment for the surfaces of the vertebrae that are engaged by the device. The spacer has mirror image convex inferior and superior load bearing or abutment surfaces adapted to engage the somewhat concave boney end plate surfaces of adjacent vertebrae. Preferably, the top and bottom convexity of the spacer between front and rear or along the central axis thereof substantially matches the concavity of the end plate surfaces whereat the spacer is to be located during usage, such that maximum surface contact occurs and so that maximum support is provided to reduce the likelihood of subsidence, while encouraging normal lordosis or kyphosis of the spinal region where the device is utilized. In particular, the convexity of the abutment surfaces peaks at a location which is somewhat anterior of a medial plane between anterior and posterior end surfaces of the interbody spacer when used to encourage normal lordosis in the lower spine.

In some embodiments the abutment surfaces may be rounded and continuous or arced from front to rear. In other embodiments, the interbody spacer has faceted abutment surfaces, each formed by a peak surface, an anterior inclined surface, and a posterior inclined surface so as to form an overall convexly arced engagement or abutment surface. The abutment surface may also include lateral bevels formed at lateral ends of the peak surface to facilitate insertion. In certain embodiments, the upper and lower surfaces can be flat, parallel to each other or higher at some point from front to rear therealong so as to form a trapezoidal or elliptical shape when viewed from the side. The upper surface can also be curvi-linear or curved in various ways so as to form a convexly rounded, oblong, tear-drop, compound curved, or otherwise shaped configuration when viewed from the side wherein the principal purpose of the upper and lower surfaces is to closely match the curvature of the vertebrae and to provide correct alignment between the opposed vertebrae.

The front or anterior and rear or posterior end surfaces are preferably planar and generally parallel and can have the same or different heights.

Lateral side surfaces of the interbody spacer are preferably partial cylindrical in shape and laterally outward opening concave to reduce volume and weight and provide a desired overall shape as well as upper and lower arches on each side of the device.

The lateral side surfaces preferably have a fixed or generally constant radius therealong generated about an axis that is parallel to a central front to rear axis of the device. Furthermore, each side surface has an inner-most region that is closest to the central axis of the device and in most embodiments is associated with a straight line or axis that extends from front to rear of the device and is parallel to the central axis of the device.

The ends of the inferior and superior abutment surfaces are spaced apart by a nominal height dimension, while the lateral surfaces are separated at their closest by a nominal width or thickness dimension. The interbody spacer of the present invention generally has a height dimension which is greater than the width dimension. Because the mutually facing surfaces of the end plates of an adjacent pair of vertebrae are concave, the peripheral edges thereof are closer than central portions of the end plate surfaces. In some embodiments the height of the device is greatest between the front and the middle of the device. However, for certain purposes the height may be constant or the height may be greatest at or near the front or any location therealong.

The spacer device has a central body or core that is solid. The core is located between vertical planes that intersect with the innermost portion of the concave side surfaces as well as the inferior and superior surfaces and the core extends between anterior and posterior ends of the device. By the term "solid" is meant that the core is free of pass through apertures, bores, windows or the like that are drilled, milled, molded, machined or otherwise made or manufactured in the core. Furthermore, the term "solid" means that any planar cut that is made in the device that is perpendicular to the central front to rear axis of the device produces a cross-section that is free of man-made voids that pass through the device. It is noted that the core can be manufactured with materials such as human bone or coral that has a certain amount of inherent porosity and still be considered solid as used herein. The core may also have shallow non-passthrough indents, knurling or grooves for tool gripping and likewise be considered solid as used herein.

The present invention includes a method of implanting interbody spacers comprising spreading the adjacent pair of vertebrae a distance somewhat greater than the width of the interbody spacer, insertion of the spacer into the intervertebral space in an orientation with the lateral side surfaces of the spacer facing the end plates of the adjacent vertebrae and thereafter rotation of the spacer about a longitudinal axis to orient the abutment surfaces into facing relation relative to the end plates of the vertebrae. The vertebrae are then allowed to seat on the abutment surfaces. The position of the spacer may then be adjusted as necessary and spinal fusion promoting bone material positioned between the vertebrae and about the device. In some methods of use, only a single spacer is used with other posterior implant support structure. In other circumstances, it is desirable to implant a pair of laterally spaced interbody spacers between the vertebrae for additional stability and strength.

Preferably, the spacer is used in conjunction with other implants including bone screws mounted in the vertebrae that are securely attached at the end of the implantation procedure to a rod or rods that extend along the spine. The bone screws and, consequently, the associated vertebrae are positioned at the end of the implantation procedure so as to urge the vertebrae into engagement with the spacer and thereby secure the position of the spacer and help or cooperate with the spacer to favorably adjust the lordosis or kyphosis of the vertebrae, while securely locating the adjacent vertebrae relative to one another so as to promote fusion.

Interbody devices of the type used herein must be compatible with implantation in the human body. Such devices include biologically active implants such as made of boney material, coral or other biologically active material where the vertebral bone eventually grows through the material of the implant, and over time replaces part or all of the implant by creeping substitution, and biologically inactive materials such as metals, plastics and the like.

OBJECTS AND ADVANTAGES OF THE INVENTION

Therefore, the objects of the present invention include: providing an interbody spacer or fusion cage device having a solid central core and concave lateral side surfaces for implanting between a pair of spaced and facing vertebrae to properly separate and align the vertebrae and/or to promote fusion between the vertebrae; providing such a device having upper and lower surfaces that preferably follow a contour of an end plate of each vertebrae and, when used in the lower spine, in which the peak of convexity of the abutment surfaces is positioned somewhat anterior of a medial plane midway between anterior and posterior end surfaces of the spacer to promote desired curvature of the spine; providing such a device in which convex abutment surfaces are formed by planar facets, including at least a peak facet, an anterior inclined facet, and a posterior inclined facet, all as a single unit or unitary piece; providing such a device formed of a material which is appropriate to the long term disposition of the device desired, such as a biologically inactive metallic material, a biologically inactive non-metallic material, a biologically active bone-based material, or a biologically active non-bone-based material; providing such a device wherein the concave lateral or side surfaces are partial cylindrically shaped and face laterally outward; providing such a device wherein the lateral side surfaces join the upper and lower abutment surfaces on opposite lateral sides of the device forming upper and lower arches on each side thereof; providing such a device wherein the structure of the interbody spacer device is strong utilizing the strength and support of the curved design for the side surfaces; providing such a device that provides a substantial open space, especially between a pair of devices in side by side relationship, to facilitate packing bone chips between vertebrae and subsequent fusion between the vertebrae associated with the devices; providing such an interbody spacer device which minimizes surgical alteration of the vertebral bones between which the spacer is implanted; providing a method of implanting such a device between a pair of adjacent vertebrae including spreading the adjacent vertebrae apart a distance somewhat greater than the lateral width of the spacer, insertion of the spacer between the vertebrae in a laterally tipped over orientation, and then rotating the device after placement in a desired location so as to orient the spacer to an upright position to engage the upper and lower abutment surfaces with facing end plate surfaces of the adjacent vertebrae and thereafter using other implants to urge the posteriors of the vertebrae toward one another to clamp the device in place; and to provide such a device which is economical to manufacture, which is relatively simple to implant, which is efficient in operation, and which is particularly well suited for its intended usage.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an enlarged perspective view of a convex spinal interbody spacer device embodying the present invention.

FIG. 2 is a side elevational view of the spacer device illustrating an anteriorly displaced convex peak of the device.

FIG. 3 is an end elevational view of the interbody spacer device.

FIG. 4 is a fragmentary elevational view at a reduced scale of the device and illustrates the device implanted between an adjacent pair of vertebrae.

FIG. 5 is a cross-sectional top plan view of the interbody spacer device implanted between the pair of vertebrae.

FIG. 10 is a view similar to FIG. 4 and illustrates the interbody spacer device implanted between an adjacent pair of vertebrae and the posterior spacing between the vertebrae comparatively reduced by manipulation of bone screws along rods.

FIG. 11 is a view similar to FIG. 5 and illustrates a an alternative use embodiment with a pair of the interbody spacer devices positioned slightly angled relative to each other in side by side relation between a pair of vertebrae.

DETAILED DESCRIPTION OF THE INVENTION

Figure 6:
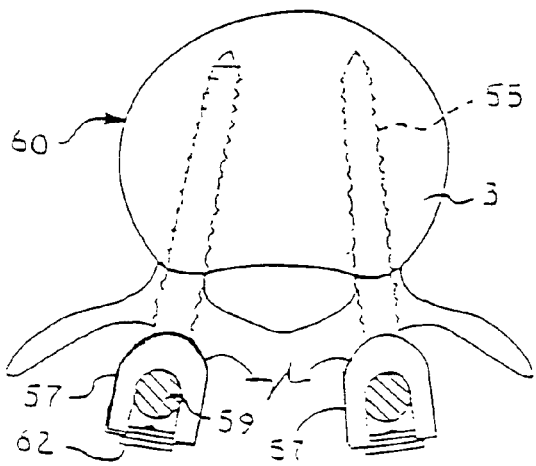
FIG. 6 is a view similar to FIG. 5 without a spacer device and illustrates details of spinal fixation structure which supports the implantation of the interbody spacer device of the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a convex spinal fusion interbody spacer device which embodies the present invention. The device 1 is used to maintain proper spacing between a pair of adjacent vertebrae 3 and 4 of a human spine as a replacement for the intervertebral disc and to promote fusion between the vertebrae 3 and 4, preferably in conjunction with other implants, as noted below.

In particular, the device 1 has a superior (or upper) surface 6 and an inferior (or lower) surface 8 which surfaces 6 and 8 are arced or convex or effectively convex when viewed from the side, such as in FIG. 2. The convexity of the abutment or load bearing surfaces 6 and 8 is fixed or rigid and generally conforms to the natural concavity of the mutually facing surfaces 10 and 12 of end plates of the adjacent vertebrae 3 and 4.

The device 1 is constructed from a single, unitary and rigid blank and has a fixed shape that is medially bowed outwardly at the top and bottom, preferably forward of a front to rear center of the device 1 for devices used in the lower spine, as discussed below. It is foreseen that in some embodiments the device 1 may be tear shaped, fish shaped, elliptical, curvilinear, oblong, fusiform or the like in nature and may have various compound curves.

Figure 7:
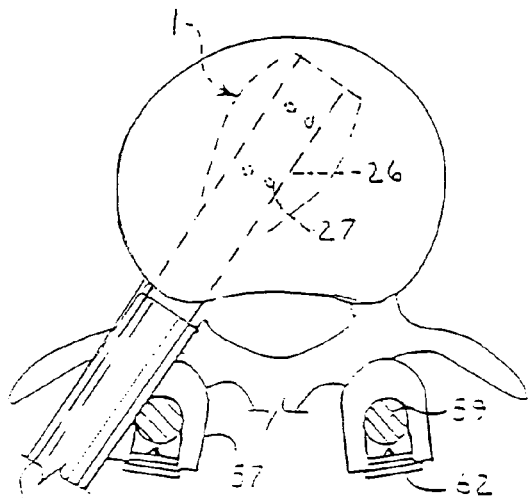
FIG. 7 is a view similar to FIG. 6 and illustrates a spacer installation tool used to implant an interbody spacer device in a orientation between an adjacent pair of the vertebrae.
Figure 8:
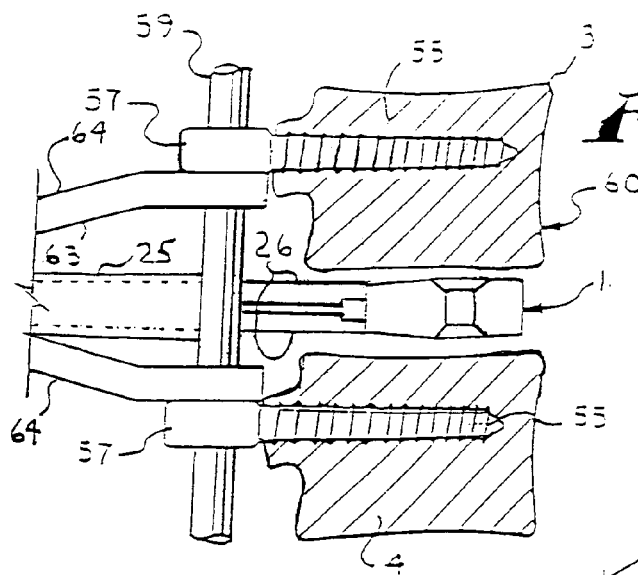
FIG. 8 is a fragmentary side elevational view illustrating the spacer installation tool with an interbody spacer device still joined thereto with portions broken away to show detail thereof.

The illustrated spacer device 1 includes front and back regions 16 and 17. The front region 16 and back region 17 have respective anterior and posterior outer end surfaces 21 and 23. The end surfaces 21 and 23 are illustrated as planar, although it is foreseen that they could be an alternative shape. The illustrated spacer device 1 includes tool engagement formations or indentations 24 to enable positive engagement by an installation tool 25 (FIGS. 7 and 8). The installation tool 25 has a pair of front hands or paddles 26 with small projection 27 that are sized, shaped and positioned to be received in the indentations 24.

The preferred spacer device 1 of the present invention for use in the lower spine is not symmetrical, when viewed from the side. FIG. 2 illustrates a front to rear middle plane 30 positioned halfway between the end surfaces 21 and 23 and parallel thereto, which bisects the device 1 from front to back with the front or anterior end thereof being to the right in FIG. 2. Also illustrated is a "convexity" plane 32 positioned at a medial location of the peak convexity of the abutment surfaces 6 and 8, thus, representing the location of such peak convexity. The imaginary convexity plane 32 is located in spaced relationship to the end surfaces 21 and 23 such that the vertical height of the device 1 at the location of the plane 32 is greater than the height of either end surface 21 or 23. In the illustrated embodiment the height of the end surfaces 21 and 23 is essentially the same, although it is foreseen that one may have a greater height than the other. It is especially noted that the front end surface 21 may have a height greater than the rear end surface 23. Also, it is foreseen that the height may be the same throughout the device 1 or the height may be greatest at any location therealong in order to satisfy the requirements for a particular usage.

In particular, as illustrated, the convexity plane 32 is positioned closer to the anterior end surface 21 (about 40% of total length from anterior end to plane 32) than to the posterior end surface 23 and is, thus, spaced anteriorly of the middle plane 30. The reason for the anteriorly shifted or displaced asymmetry of the convexity of the present embodiment is to more closely conform the shape of the abutment surfaces 6 and 8 to the concavity of the vertebral end plate surfaces 10 and 12 while adjusting the relative positions of the vertebrae 3 and 4, so as to preferably correct lordotic alignment of the vertebrae 3 and 4. Such shape conformance respectively between the abutment surfaces 6 and 8 and the vertebral surfaces 10 and 12 tends to maximize load bearing engagement therebetween through comparatively greater surface contact and tends to minimize possible subsidence of the device 1 into the vertebrae 3 and 4, while providing greater spacing between the anterior ends of the vertebrae 3 and 4 than the posterior ends thereof (see FIG. 9).

The illustrated abutment surfaces 6 and 8 are formed by multiple component surfaces or facets, including a peak facet 35, an anterior or front facet 36, and a posterior or rear facet 37. However, it is foreseen in certain circumstances that the surfaces 6 and 8 may be formed by a continuous or even a discontinuous curved surface or by other suitable elements forming a surface that will generally conform to the concavity of the lower and upper surface of the vertebrae 3 and 4 respectfully from both back to front and from side to side. The surfaces 6 and 8 may also include lateral facets or bevels 38. In certain embodiments it is foreseen that the sides of the upper and lower surfaces 6 and 8 may be curved or radiused to meet the sides of the device 1 to promote rotation during installation. Because the plane of convexity 32 is displaced anteriorly of the middle plane 30, the anterior facet 36 is shorter than the posterior facet 37. When designed for use in the upper (thoracic) spine the preferred shape may be reversed as compared to the lower (lumbar) spine.

As noted above the illustrated abutment surfaces 6 and 8 are faceted, but such could alternatively be formed by continuous, curved surfaces, either with a continuous radius, a continuous curve or a combination of curves. Additionally, the abutment surfaces 6 and 8 may be somewhat more easily and more accurately formed by the facets 35-38 in a machining process than would be possible with a compound curved contour of the surfaces 6 and 8.

Referring to FIGS. 1 and 3, the interbody spacer device 1 has side or lateral surfaces 42 and 43. The side surfaces 42 and 43 open laterally outward in opposite directions. In the illustrated embodiment the indentations 24 are located in the side surfaces 42 and 43. The innermost region of each side surface 42 and 43 (that is, the closest to a central front to rear axis 50) defines a line or axis 51 which is parallel to the central axis 50. The side surfaces 42 and 43 are partially cylindrical or concave in shape and extend parallel to the front to rear axis 50. The concavity of the surfaces 42 and 43 results in a weight reduction in the device 1 without appreciably reducing its strength.

Preferably each side surface 42 and 43 has a generally constant radius throughout and extends from near the superior surface 6 to near the inferior surface 7. However, it is foreseen that in some embodiments that a radius that is not constant throughout may be used.

The device 1 has a central body or core 52 that is located between superior and inferior surfaces 6 and 8, between end walls 16 and 17 and between vertical planes passing through axes 51. The core 52 is free of pass through bores, windows, fenestrations, cavities or the like but may include the tool gripping apertures 24, so as to form a solid and relatively strong central structure for the device 1. The intersection of the side surfaces 42 and 43 with the body 52 form upper and lower arches 53 on each side of the device 1.

The device 1 can be formed from any material which has suitable structural properties, which is biologically non harmful, and which does not promote the growth of pathogens. The material of construction can be biologically active or inactive as discussed in greater detail below. For example, various types of stainless steel are suitable as materials of construction. The device 1 can be formed by molding, by machining, cutting, milling, or the like, or by a combination of such processes to preferably form a single or unitary structure, preferably with no parts that are moveable relative to other parts thereof.

The present invention includes novel methods of implanting a spinal fusion spacer device 1 between a pair of adjacent vertebrae 3 and 4. Referring to FIG. 3, the device 1 has a height dimension measured between the upper and lower peak facets 35 and a width or thickness dimension represented by the facets 36 or 37 at their widest. As can be observed from the frontal view shown in FIG. 3, the height dimension of the device 1 exceeds the width thereof by a considerable extent. In the illustrated embodiment the height at plane 32 is about 2.3 times the maximum side to side width. It should be noted that the upright orientation of the device 1 shown in FIGS. 1-5 and 9-11 is the operational orientation of the spacer device 1 in which the device 1 performs the function thereof as a spacer between the vertebrae 3 and 4.

As stated previously, the facing surfaces 10 and 12 of the vertebrae 3 and 4 are somewhat concave in that most of the interior or central regions 46 (FIG. 10) of the surfaces 10 and 12 are spaced farther apart than edge regions 48 of the surfaces 10 and 12. In order to implant a device 1 between the vertebrae 3 and 4, it is preferable to position the vertebrae 3 and 4 far enough apart so that the device 1 can be inserted therebetween at least sideways and then rotated. Insertion is most often by a posterior approach, but may be from any direction selected by the surgeon.

In the illustrated embodiment, the vertebrae 3 and 4 are spread apart during the surgical procedure a sufficient distance that the device 1 can be inserted between the edge regions 48 in a laterally laid-over or tipped-over orientation (see FIGS. 7 and 8) and then rotated to the upright orientation shown particularly in FIGS. 1, 4, and 10. The device 1 is inserted between the vertebrae 3 and 4 in the tipped-over orientation to the eventual use location thereof and then rotated only ninety degrees (as opposed to screwing multiple full turns into place as is the case of many cylindrical screw in type devices) about the longitudinal axis 50 (FIG. 1).

Most specifically, with respect to the procedure and referring to FIGS. 5-9, a pair of open-headed bone screws 55 are threadedly implanted into each of the vertebrae 3 and 4. Open heads 57 of the screws 55 are aligned to receive spinal fixation rods 59 which run lengthwise along at least a portion of the spine 60 of which the vertebrae 3 and 4 are components. The bone screw heads 57 receive closure plugs 62 which capture the rods 59 and, when tightened, secure the rods 59 within the heads 57 against relative movement. The heads 57 and plugs 62 may employ cooperating helical guide and advancement mechanisms to advance the plugs 62 into engagement with the rods 59, as the plugs 62 are rotated into the heads 57, such as threads or flange forms. Details of open-headed bone screws 55 and closure plugs 62 which would be appropriate for use with the device 1 can found in U.S. Pat. No. 6,004,349, which is incorporated herein by reference. Initially the rods 59 are captured only loosely in the heads 57 by the plugs 62, so as to allow movement of the screws 55 along the rods 59 under control of the surgeon.

The vertebrae 3 and 4 are spaced a desired distance by use of a scissors like spreader tool 63 (partially seen in FIG. 8) having arms 64, and the plugs 62 may be lightly tightened into engagement with the rods 59. The desired intervertebral distance is such a distance which enables insertion of the spacer device 1 therebetween in the tipped-over orientation (FIG. 8) and then uprighting of the device 1 (FIG. 10) by ninety degree rotation and reorientation to the upright orientation. The spacer device 1 is inserted between the spread vertebrae 3 and 4 in the tipped-over orientation and rotated to the upright orientation using the installation tool 25; then the tool 25 is detached from the device 1. In certain embodiments, the tool 25 and the device 1 are cooperatively constructed such that when the tool 25 is gripping the device 1, the maximum overall width between the outside of the paddles 26 does not exceed the maximum side to side width of the device 1, see FIG. 8.

Figure 9:
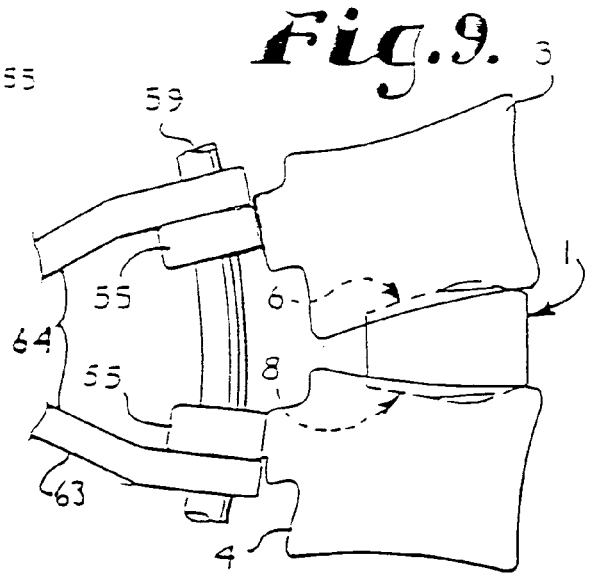
FIG. 9 is a view similar to FIG. 8 and illustrates the interbody spacer device rotated ninety degrees to an upright orientation and spinal fixation rods compressed to position the adjacent vertebrae in a desired final relationship.

The plugs 62 are then loosened and the tool 63 is used as a compression tool (see FIG. 9) to urge the screws 55 of adjacent vertebrae 3 and 4 toward each other so that the posterior ends of the vertebrae 3 and 4 become more closely spaced to allow the inner surfaces 10 and 12 respectively thereof to engage the upper and lower abutment surfaces 6 and 8 of the device 1, preferably in a snug or clamping relationship. This clamping secures the device 1 in the position selected therefor between the vertebrae 3 and 4. The orientation of the device 1 about an axis parallel to the spine 60 is adjusted, if necessary prior to final tightening of the plugs 62 to lock the relative position between the rod 59 and screws 55. The rods 59 may be bent somewhat to achieve a desired angular or lordotic relationship in the lower spine or the opposite in the upper spine between the vertebrae 3 and 4, as shown in FIG. 9. A single device 1 when used in conjunction with a pair of the bone screws 55 in each vertebrae 3 and 4 forms a solid multiple location of support so as to stabilize the vertebrae 3 and 4 with respect to each other. In the illustrated embodiment there are three locations of support provided for each vertebrae 3 and 4 relative to its adjacent vertebrae 3 or 4.

In an alternative usage, illustrated in FIG. 11, the implantation procedure may also include the insertion of a second spacer device 1 between the vertebrae 3 and 4 in laterally spaced relation thereto.

When the desired degree of engagement between the vertebrae 3 and 4 and one or two of the devices 1, along with the desired orientation of the devices 1 and the vertebrae 3 and 4, the closure plugs 62 are advanced into secure engagement with the rods 59 in a substantially permanent relation. Such an embodiment provides four locations of support for each vertebrae 3 and 4 relative to the adjacent vertebrae 3 or 4.

Any voids between the vertebrae 3 and 4 and the device or devices 1 are preferably packed with bone material which, over time, will promote fusion between the vertebrae 3 and 4 in the spacing and orientations established by the spacer device 1 and the fixation rods 59.

The device 1 preferably includes no moving or adjustable parts, is non-threaded, includes no fins to cut into the bone and has no central cavity for receiving bone or the like. The device 1 may be manufactured from biologically inactive materials or from biologically active materials which are compatible with implantation. The device 1 formed of biologically inactive materials is chemically and biologically essentially inert in its implanted environments. Fusion of the vertebrae 3 and 4 occurs around the device 1; however, the device 1 remains intact after implantation. The biologically inactive materials used for the device 1 can be divided into metallic materials and non-metallic materials.

Metallic biologically inactive materials may include certain alloys of stainless steel, titanium, and tantalum and other alloys which are structurally, chemically, and biologically appropriate. Non-metallic biologically inactive materials for the device 1 can include certain plastics or polymers, organic and inorganic resins, composites, and ceramics, especially polyester ketone or the polymer commonly referred to as "peek". The polymers are preferably non-porous. The composites may include carbon fiber reinforced materials. Appropriate ceramics are preferably porous (but solid in accordance with the invention) and can be of an "open scaffold" type which allow bone fusion growth into or through the ceramic material itself.

The device 1 can also be formed from biologically active materials which are normally substituted for, absorbed, or otherwise replaced as bone fusion of the vertebrae 3 and 4 proceeds. The biologically active materials can be either bone-based or non-bone-based. The term bone-based material is used herein to refer to a material which is made from actual bones, bone derivatives, or materials which are chemically bone-like. Bones are typically formed mostly (about 85 percent) of tri-basic calcium phosphate which, in living bone, is called hydroxy-apatite or simply calcium phosphate. In general, the bone is formed by cutting, machining, milling or the like or bone derived material is ground, mixed with a suitable resin or other binder, and cast, molded or machined to shape. Further machining or other mechanical forming may be performed in final shaping of formed implant spacers. The source of bone for such material may be from the patient who will receive the implant (autograft) or from cadaver bone (allograft). Other sources may include non-human bone.

Biologically active, non-bone-based materials appropriate for use in the device 1 include corals, certain resins and similar materials. The principal constituent of coral is calcium carbonate in a porous form which allows bone fusion growth into and through the resulting spacer. The device 1 can be formed of coral by machining or carving processes. As noted, the coral material is somewhat porous and is normally replaced over time by natural biological processes in the body, as the spinal fusion process occurs.

Although the illustrated embodiment shows the device 1 being inserted fully from the posterior and then rotated ninety degrees, it is foreseen that the device 1 could be inserted anteriorly or from the side.

It is also foreseen that in certain embodiments, the greatest height of the device may especially be at an anterior end thereof, as required in some situations to produce correct spinal curvature, such that the device has a generally trapezoidal side profile.

It is to be understood that while certain forms of the present invention have been illustrated and described herein, it is not to be limited to the specific forms or arrangement of parts described and shown.

What is claimed and desired to be secured by Letters Patent is as follows:

1. An interbody spacer adapted for placement between a pair of spaced and facing vertebrae of a spine; said spacer comprising:
   a) a body having upper and lower abutment surfaces adapted to engage respective vertebrae during use and a front surface and a rear surface; said front and rear surfaces having substantially equal widths and being substantially flat and vertically aligned in use; said upper and lower abutment surfaces being generally convex from front to rear formed by a front planar facet, a middle planar facet, and a rear planar facet, wherein the middle planar facet includes opposed planar lateral bevels sloping outwardly wherein said abutment surfaces have a maximum height at a point closer to a body midline than to both said front and rear surfaces so as to be adapted to conform to the curvature of facing surfaces of the vertebrae and so as to facilitate insertion;
   b) said body having a pair of opposed concave lateral side surfaces that extend from the front to the rear thereof and include at least one tool-engagement formation wherein each of said side surfaces cooperate with said planar lateral bevels so as to facilitate rotation of the spacer during installation; and
   c) a first width of a first intersection of said front surface with each of the upper and lower abutment surfaces being substantially equal to a second width of a second intersection of said rear surface with each of the upper and lower abutment surfaces so as to resist subsidence of said body into the facing surfaces of the vertebrae; a third width of each of the upper and lower abutment surfaces being greater than the first and second widths at a location spaced from both the first and second intersections; and d) said body having a solid core located between said side surfaces.

2. The interbody spacer according to claim 1 wherein:
a) said lateral side surfaces have a generally constant radius therealong about an axis that is parallel to a front to rear central axis of said body.

3. The interbody spacer according to claim 2 wherein:
a) each of said lateral side surfaces has an innermost region; and
b) said solid core is located between vertical planes tangentially engaging the innermost region of respective lateral side surfaces; said core being further positioned between said upper and lower abutment surfaces and between said front and rear surfaces.

4. The interbody spacer according to claim 1 wherein:
a) said solid core is free of pass through apertures.

5. The interbody spacer according to claim 1 wherein:
a) said lateral side surfaces open laterally outward in opposite directions and each lateral side surface is partially cylindrical in shape about an axis that is parallel to a central front to rear axis of said body.

6. The interbody spacer according to claim 1 wherein:
a) said body has a central front to rear axis; and
b) said core at any cross section thereof that is perpendicular to said body axis is free of pass through voids.

7. The interbody spacer according to claim 1 wherein:
a) said lateral side surfaces in conjunction with the intersection thereof with said upper and lower surfaces form upper and lower arches on each side of said spacer; and
b) said arches cooperate with said central core to provide a strong stable support structure.

8. The interbody spacer according to claim 1 wherein:
a) said upper and lower abutment surfaces are substantially smooth.

9. The interbody spacer according to claim 1 wherein:
a) said body includes a plane of convexity; and
b) said plane of convexity is associated with said point closer to a body midline.

10. An interbody spacer having opposed concave side surfaces comprising:
a) a solid central core located between said side surfaces; the central core having upper and lower surfaces that are generally convex from a front to a rear of the spacer and are formed by a front planar facet, a middle planar facet, and a rear planar facet; the core having front and rear surfaces that are generally flat and vertical in use and that intersect at opposite ends with the upper and lower surfaces at intersections; all of the intersections are of generally equal width and each of the upper and lower surfaces are wider than the intersections at a location spaced from both of the intersections;
b) each of said upper and lower surfaces having opposed planar lateral bevels sloping outwardly and cooperating with side surfaces and being adapted to facilitate rotation of the spacer during installation; the upper and lower surfaces having a maximum height spaced nearer to a center of the spacer than to any of the intersections; and
c) said side surfaces open laterally outward and have a generally uniform radius therealong; said side surfaces extending from near the upper surface to near the lower surface of said core; said side surfaces having an axis that is generally paralleled to a central front to rear axis of said core; and said side surfaces having at least one tool-engagement formation, wherein said at least one tool-engagement formation extends laterally from said side surface in a direction selected from the group consisting of inward and outward.

11. A method of promoting fusion between a pair of spaced and facing vertebrae comprising the steps of:
a) providing an interbody spacer having a body with a solid central core located between a pair of opposed and concave lateral side surfaces that extend from a front to a rear of the body and having a pair of upper and lower convex surfaces that are convex between the front and the rear of the body formed by a front planar facet, a middle planar facet, and a rear planar facet and that are adapted to conform to the curvature of facing surfaces of the facing vertebrae; the body having front and rear surfaces that are generally flat and vertical in use and that intersect with the upper and lower surfaces at intersections that are all substantially equal in width; said central core having a maximum height near a midpoint thereof and spaced from each of the intersections; the upper and lower surfaces being widest at a location spaced from opposite ends thereof and each of said side surfaces having at least one tool-engagement formation extending inwardly therefrom and being adapted to cooperatively engage engagement pins of an installation tool;
b) providing laterally positioned bevels on opposed sides of the middle facet of each of the upper and lower surfaces;
c) placing said spacer in a sideways position between said vertebrae;
d) rotating said spacer to an upright position so that the bevels facilitate rotation of the spacer and so that the upper and lower surfaces are aligned after rotation with and in touching relationship with similarly shaped facing surfaces of the vertebrae; and
e) thereafter supporting one of said vertebrae relative to the other with said spacer so as to encourage fusion of bone between said vertebrae.

12. An interbody spacer adapted for placement between a pair of spaced and facing vertebrae of a spine; said spacer comprising:
a) a body having upper and lower abutment surfaces adapted to engage respective vertebrae during use and a front surface and a rear surface; said front and rear surfaces being generally vertical and flat during use; said upper and lower abutment surfaces being generally convex from front to rear wherein said abutment surfaces are formed by a front planar facet, a middle planar facet, and a rear planar facet and have a maximum height at a point closer to a body midline than to both said front and rear surfaces so as to be adapted to conform to the curvature of facing surfaces of the vertebrae and so as to facilitate insertion, said body including an intersection between each of said upper and lower abutment surfaces and each of said front and rear surfaces, each of said intersections including a width, said widths being substantially equal to one another and being spaced from the maximum height; both of the upper and lower abutment surfaces being wider at a location spaced from both of the intersections than at the intersections;

b) at least one lateral facet joined to and sloping laterally away from the middle facet of at least a respective one of the upper and lower abutment surfaces;

c) said body having a pair of opposed concave lateral side surfaces that extend from the front to the rear thereof and include at least one tool-engagement formation; and d) said body having a solid core located between said side surfaces.

13. An interbody spacer adapted for placement between a pair of spaced and facing vertebrae of a spine; said spacer comprising:

a) a body having upper and lower abutment surfaces adapted to engage respective vertebrae during use and a front surface and a rear surface the front and rear surfaces being substantially flat and vertical in use; said front and rear surfaces intersecting with the upper and lower abutment surfaces at intersections; said upper and lower abutment surfaces being generally convex from front to rear wherein said abutment surfaces have a maximum height at a point closer to a body midline than to said front surface and being substantially spaced from both the front and rear surfaces so as to be adapted to conform to the curvature of facing surfaces of the vertebrae and so as to facilitate insertion; each of the upper and lower abutment surfaces being formed by a front planar facet, a middle planar facet and a rear planar facet wherein the middle planar facet includes opposed planar lateral bevels sloping outwardly;

b) said body having a pair of opposed concave lateral side surfaces that extend from a front to a rear thereof and include at least one tool-engagement formation wherein each of said side surfaces cooperate with said planar lateral bevels so as to facilitate rotation of the spacer during installation; and c) a width of the intersection of said front surface with each of upper and lower abutment surfaces being substantially equal to a width of the intersection of said rear surface with each of upper and lower abutment surfaces so as to resist subsidence of said body into the facing surfaces of the vertebrae; both of the upper and lower abutment surfaces being wider at a location spaced from both of the intersections than at the intersections; and d) said body having a solid core located between said side surfaces.

14. An interbody spacer adapted for placement between a pair of spaced and facing vertebrae of a spine; said spacer comprising:

a) a body having upper and lower abutment surfaces adapted to engage respective vertebrae during use and a front surface and a rear surface; the front and rear surfaces being substantially flat and vertical in use and intersecting the upper and lower abutment surfaces respectfully at intersections; said upper and lower abutment surfaces being generally convex from front to rear wherein said abutment surfaces have a maximum height at a point closer to a body midline than to said front surface and where the maximum height is substantially spaced from each intersection so as to be adapted to conform to the curvature of facing surfaces of the vertebrae and so as to facilitate insertion; the upper and lower abutment surfaces each comprising a front planar facet, a middle planar facet and a rear planar facet joined so as to be convex; the upper and lower abutment surfaces each having opposed side bevels located between the front and rear surfaces to facilitate turning of the body during installation;

b) said body having a pair of opposed concave lateral side surfaces that cooperate with said side bevels, extend from the front to the rear thereof and include at least one tool-engagement formation; the side surfaces extend between the upper and lower abutment surfaces and are concave having an axis of curvature that extends from front to rear; and c) a first width of a first intersection of said front surface with each of upper and lower abutment surfaces being substantially equal to a second width of a second intersection of said rear surface with each of upper and lower abutment surfaces so as to resist subsidence of said body into the facing surfaces of the vertebrae; each of the upper and lower abutment surfaces having a third width spaced from the first and second widths that is wider than the first and second widths; and d) said body having a solid core located between said side surfaces.

\* \* \* \* \*